United States Patent [19]

Baker et al.

[11] Patent Number: 5,576,336
[45] Date of Patent: Nov. 19, 1996

[54] INDOLE DERIVATIVES AS DOPAMINE $D_4$ ANTAGONISTS

[75] Inventors: Raymond Baker, Green Tye; Howard B. Broughton, Harlow; Janusz J. Kulagowski, Bishops Stortford; Paul D. Leeson, Cambridge; Ian M. Mawer, Bishops Stortford, all of Great Britain

[73] Assignee: Merck Sharp & Dohme Limited, Hoddesdon, England

[21] Appl. No.: 525,695

[22] PCT Filed: Mar. 16, 1994

[86] PCT No.: PCT/GB94/00527

§ 371 Date: Sep. 13, 1995

§ 102(e) Date: Sep. 13, 1995

[87] PCT Pub. No.: WO94/21627

PCT Pub. Date: Sep. 29, 1994

[30] Foreign Application Priority Data

Mar. 18, 1993 [GB] United Kingdom ............... 9305642
Aug. 10, 1993 [GB] United Kingdom ............... 9316627

[51] Int. Cl.⁶ .................. A61K 31/40; C07D 211/14
[52] U.S. Cl. ........................... 514/323; 546/201
[58] Field of Search ..................... 514/323; 546/201

[56] References Cited

U.S. PATENT DOCUMENTS

Re. 28,973 9/1976 Welstead, Jr. .................. 546/201

FOREIGN PATENT DOCUMENTS

0449186A2 10/1991 European Pat. Off. .
61-227565 10/1986 Japan .
64-52718 2/1989 Japan .
2083476 3/1982 United Kingdom .

*Primary Examiner*—C. Warren Ivy
*Assistant Examiner*—Garth M. Dahlen
*Attorney, Agent, or Firm*—Robert J. North; Melvin Winokur

[57] ABSTRACT

Compounds of formula (I), or a salt or prodrug thereof, wherein R represent hydrogen or $C_{1-6}$ alkyl; Q represents a moiety of formula Qa or Qb; they are antagonists of dopamine receptor subtypes within the brain, having a selective affinity for the dopamine $D_4$ receptor subtype over other dopamine receptor subtypes, and are accordingly of benefit in the treatment and/or prevention of psychotic disorders such as schizophrenia whilst manifesting fewer side-effects than those associated with classical neuroleptic drugs.

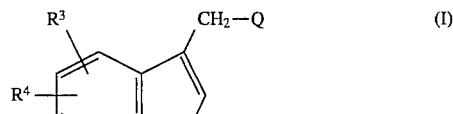

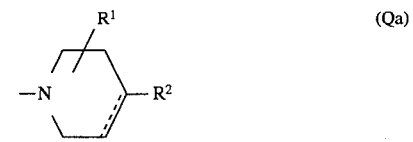

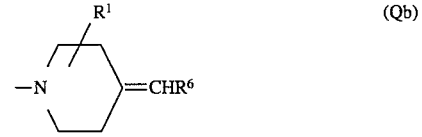

9 Claims, No Drawings

INDOLE DERIVATIVES AS DOPAMINE D$_4$ ANTAGONISTS

This is the national stage application of PCT/GB94/00527 filed Mar. 16, 1994 and published as WO94/21627 Sep. 29, 1994.

This invention relates to a particular class of heteroaromatic compounds. More particularly, the invention is concerned with the use of substituted indole derivatives which are antagonists of dopamine receptor subtypes within the brain and are therefore of benefit in the treatment and/or prevention of psychotic disorders such as schizophrenia.

The "dopamine hypothesis" of schizophrenia predicts an increased activity of dopamine neurotransmission in the disease. The hypothesis is supported by early observations that drugs, such as amphetamine, with dopamine agonist or dopamine-releasing properties are capable of eliciting a psychosis indistinguishable from acute paranoid schizophrenia.

Schizophrenia is a disorder which is conventionally treated with drugs known as neuroleptics. In the majority of cases, the symptoms of schizophrenia can be treated successfully with so-called "classical" neuroleptic agents such as haloperidol. Classical neuroleptics generally are antagonists at dopamine D$_2$ receptors. The fact that classical neuroleptic drugs have an action on dopamine receptors in the brain thus lends credence to the "dopamine hypothesis" of schizophrenia.

Molecular biological techniques have revealed the existence of several subtypes of the dopamine receptor. The dopamine D$_1$ receptor subtype has been shown to occur in at least two discrete forms. Two forms of the D$_2$ receptor subtype, and at least one form of the D$_3$ receptor subtype, have also been discovered. More recently, the D$_4$ (Van Tol et al., *Nature* (London), 1991, 350, 610) and D$_5$ (Sunahara et al., *Nature* (London), 1991, 350, 614) receptor subtypes have been described.

Notwithstanding their beneficial antipsychotic effects, classical neuroleptic agents such as haloperidol are frequently responsible for eliciting acute extrapyramidal symptoms and neuroendocrine disturbances. These side-effects, which clearly detract from the clinical desirability of classical neuroleptics, are believed to be attributable to D$_2$ receptor blockade in the striatal region of the brain. It is considered (Van Tol et al., supra) that compounds which can interact selectively with the dopamine D$_4$ receptor subtype, whilst having a less-pronounced action at the D$_2$ subtype, might be free from, or at any rate less prone to, the side-effects associated with classical neuroleptics, whilst at the same time maintaining a beneficial level of antipsychotic activity.

The compounds in accordance with the present invention, being antagonists of dopamine receptor subtypes within the brain, are accordingly of benefit in the treatment and/or prevention of psychotic disorders such as schizophrenia. Moreover, the compounds according to the invention have a selective affinity for the dopamine D$_4$ receptor subtype over other dopamine receptor subtypes, in particular the D$_2$ subtype, and can therefore be expected to manifest fewer side-effects than those associated with classical neuroleptic drugs.

In GB-A-2083476 there is described inter alia a class of 3-[piperidin-1-ylmethyl]-1H-indole and 3-[1,2,3,6-tetrahydropyrid-1-ylmethyl]-1H-indole derivatives, substituted at the 4-position respectively of the piperidine or tetrahydropyridine moiety by an optionally substituted phenyl group. These compounds are stated to exhibit psychotropic activity and, in some cases, anti-depressant activity. There is, however, no suggestion in GB-A-2083476 that the compounds described therein might be antagonists of dopamine receptor subtypes within the brain, and thus be of benefit in the treatment and/or prevention of psychotic disorders such as schizophrenia, still less that in doing so they might be expected to manifest fewer side-effects than those exhibited by classical neuroleptic agents. Indeed, certain of the compounds described in GB-A-2083476 are explicitly stated to show dopamine agonist activity.

The generic disclosure of EP-A-0449186 encompasses inter alia a series of substituted piperidin-1-ylalkyl-indole derivatives which are stated to be antipsychotic agents that act by selective antagonism of the sigma receptor. There is, however, no specific disclosure therein of a [4-substituted-piperidin-1-ylmethyl]-1H-indole derivative. Moreover, there is no suggestion in EP-A-0449186 that the compounds described therein might solve the problem of providing antagonists of dopamine receptor subtypes within the brain, in particular agents having a selective affinity for the dopamine D$_4$ receptor subtype over other dopamine receptor subtypes. Indeed, it is explicitly stated in EP-A0449186 that the compounds described therein do not bind to the dopamine receptors or only have weak binding for the dopamine receptors.

JP-A-61-227565 and JP-A-64-52718 describe in generic terms various [4-substituted-piperidin-1-yl-alkyl]-indole derivatives, which are stated to be effective against certain cardiovascular complaints. There is, however, no suggestion in either of these publications that the compounds described therein might be of benefit in the treatment and/or prevention of disorders of the central nervous system, in particular psychotic disorders such as schizophrenia.

The present invention accordingly provides a compound of formula I, or a salt or prodrug thereof:

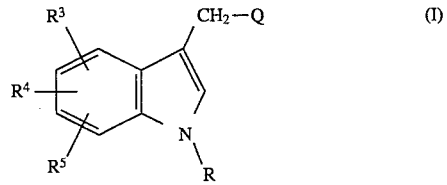

wherein

R represents hydrogen or C$_{1-6}$ alkyl;

Q represents a moiety of formula Qa or Qb:

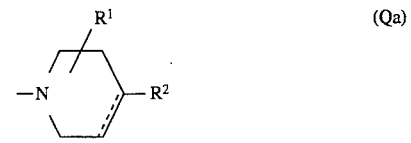

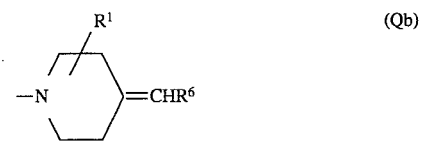

in which the broken line represents an optional chemical bond;

R$^1$ represents hydrogen, or an optionally substituted C$_{1-6}$ alkyl, C$_{1-6}$ alkoxy, C$_{2-6}$ alkenyl, C$_{2-6}$ alkynyl, aryl, aryl (C$_{1-6}$) alkyl, aryloxy (C$_{1-6}$) alkyl, aryl (C$_{1-6}$) alkoxy, aryl (C$_{1-6}$) alkylthio, aryl (C$_{2-6}$) alkenyl, aryl (C$_{2-6}$) alkynyl, C$_{3-7}$ heterocycloalkyl (C$_{1-6}$) alkyl, heteroaryl, heteroaryl (C$_{1-6}$) alkyl, heteroaryl (C$_{2-6}$) alkenyl or heteroaryl (C$_{2-6}$) alkynyl group;

R$^2$ represents an optionally substituted C$_{1-6}$ alkoxy, C$_{2-6}$ alkenyl, C$_{2-6}$ alkynyl or C$_{3-7}$ heterocycloalkyl (C$_{1-6}$) alkyl group; or aryl (C$_{2-6}$) alkyl, aryloxy (C$_{1-6}$) alkyl, aryl (C$_{1-6}$) alkoxy, aryl (C$_{1-6}$)alkylthio, aryl (C$_{2-6}$)alkenyl, aryl (C$_{2-6}$)alkynyl, heteroaryl (C$_{2-6}$)alkyl, heteroaryl (C$_{2-6}$) alkenyl or heteroaryl ($C_{2-6}$) alkynyl, any of which groups may be optionally substituted on the aromatic moiety;

$R^6$ represents an optionally substituted $C_{1-6}$ alkyl, $C_{1-6}$ alkoxy, $C_{2-6}$ alkenyl, $C_{2-6}$ alkynyl, aryl, aryl ($C_{1-6}$) alkyl, aryloxy ($C_{1-6}$) alkyl, aryl ($C_{1-6}$) alkoxy, aryl ($C_{1-6}$)alkylthio, aryl ($C_{2-6}$)alkenyl, aryl ($C_{2-6}$) alkynyl, $C_{3-7}$ heterocycloalkyl ($C_{1-6}$) alkyl, heteroaryl, heteroaryl ($C_{1-6}$) alkyl, heteroaryl ($C_{2-6}$) alkenyl or heteroaryl ($C_{2-6}$) alkynyl group;

$R^3$, $R^4$ and $R^5$ independently represent hydrogen, hydrocarbon, a heterocyclic group, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$ or —$CONR^aR^b$; and $R^a$ and $R^b$ independently represent hydrogen, hydrocarbon or a heterocyclic group.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl, aryl($C_{1-6}$)alkyl, aryl($C_{2-6}$)alkenyl and aryl($C_{2-6}$)alkynyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include $C_{3-7}$ heterocycloalkyl, $C_{3-7}$ heterocycloalkyl($C_{1-6}$)alkyl, heteroaryl, heteroaryl($C_{1-6}$)alkyl, heteroaryl($C_{2-6}$)alkenyl and heteroaryl($C_{2-6}$)alkynyl groups.

Suitable alkyl groups within the scope of the term "hydrocarbon" and within the definition of the substituents R, $R^1$ and $R^6$ include straight-chained and branched alkyl groups containing from 1 to 6 carbon atoms. Typical examples include methyl and ethyl groups, and straight-chained or branched propyl and butyl groups. Particular alkyl groups are methyl, ethyl, n-propyl, isopropyl and t-butyl.

Suitable alkenyl groups within the scope of the term "hydrocarbon" and within the definition of the substituents $R^1$, $R^2$ and $R^6$ include straight-chained and branched alkenyl groups containing from 2 to 6 carbon atoms. Typical examples include vinyl and allyl groups.

Suitable alkynyl groups within the scope of the term "hydrocarbon" and within the definition of the substituents $R^1$, $R^2$ and $R^6$ include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Particular aryl groups within the scope of the term "hydrocarbon" and within the definition of the substituents $R^1$ and $R^6$ include phenyl and naphthyl.

Particular aryl-alkyl groups within the scope of the term "hydrocarbon" and within the definition of the substituents $R^1$, $R^2$ and $R^6$ include benzyl, naphthylmethyl, phenethyl and phenylpropyl.

A particular aryl($C_{2-6}$)alkenyl group within the scope of the term "hydrocarbon" and within the definition of the substituents $R^1$, $R^2$ and $R^6$ is phenylethenyl.

A particular aryl($C_{2-6}$)alkynyl group within the scope of the term "hydrocarbon" and within the definition of the substituents $R^1$, $R^2$ and $R^6$ is phenylethynyl.

Suitable heterocycloalkyl groups include azetidinyl, pyrrolidyl, piperidyl, piperazinyl, morpholinyl and tetrahydrofuryl groups.

A particular $C_{3-7}$ heterocycloalkyl($C_{1-6}$)alkyl group within the scope of the expression "a heterocyclic group" and within the definition of the substituents $R^1$, $R^2$ and $R^6$ is tetrahydrofurylethyl.

Suitable heteroaryl groups within the scope of the expression "a heterocyclic group" and within the definition of the substituents $R^1$ and $R^6$ include pyridyl, quinolyl, isoquinolyl, pyridazinyl, pyrimidinyl, pyrazinyl, pyranyl, furyl, benzofuryl, dibenzofuryl, thienyl, benzthienyl, indolyl, indazolyl, imidazolyl, benzimidazolyl, oxadiazolyl and thiadiazolyl groups.

Particular heteroaryl-alkyl groups within the scope of the expression "a heterocyclic group" and within the definition of the substituents $R^1$, $R^2$ and $R^6$ include thienylmethyl, thienylethyl, furylethyl, pyridylmethyl, pyridylethyl, pyrimidinylmethyl and pyrazinylmethyl.

The hydrocarbon and heterocyclic groups, as well as the substituents $R^1$, $R^2$ and $R^6$, may in turn be optionally substituted by one or more groups selected from $C_{1-6}$ alkyl, adamantyl, phenyl, aryl($C_{1-6}$)alkyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, trifluoromethanesulphonyloxy, —$NR^vR^w$, —$NR^vCOR^w$, —$NR^vCO_2R^w$, —$NR^vSO_2R^w$, —$CH_2NR^vSO_2R^w$, —$NHCONR^vR^w$, —$PO(OR^v)(OR^w)$, —$CONR^vR^w$, —$SO_2NR^vR^w$ and —$CH_2SO_2NR^vR^w$, in which $R^v$ and $R^w$ independently represent hydrogen, $C_{1-6}$ alkyl, aryl or aryl($C_{1-6}$)alkyl.

The term "halogen" as used herein includes fluorine, chlorine, bromine and iodine, especially chlorine.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof are encompassed within the scope of the present invention.

Suitably, the substituent R represents hydrogen or methyl, especially hydrogen.

Suitably, the substituent $R^1$ represents hydrogen.

Suitably, the substituent $R^2$ represents aryl($C_{2-6}$)alkyl, aryloxy($C_{1-6}$)alkyl, aryl($C_{1-6}$)alkoxy, aryl($C_{1-6}$)alkylthio, aryl($C_{2-6}$)alkenyl, aryl($C_{2-6}$)alkynyl or heteroaryl($C_{2-6}$)alkyl, any of which groups may be optionally substituted on the aromatic moiety. Examples of optional substituents on the group $R^2$ include $C_{1-6}$ alkyl, halogen, trifluoromethyl, $C_{1-6}$ alkoxy, nitro, $C_{1-6}$ alkylamino and di($C_{1-6}$)alkylamino. Particular values of $R^2$ include phenethyl, phenylpropyl, phenoxymethyl, benzyloxy, benzylthio, phenylethenyl, phenylethynyl and furylethyl.

Suitable values for the substituents $R^3$, $R^4$ and $R^5$ include hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$)alkoxy and $C_{2-6}$ alkylcarbonyl. Particular values include hydrogen, fluoro, chloro, methyl, methoxy and benzyloxy.

Suitably, the substituent $R^6$ represents aryl($C_{1-6}$)alkyl, especially benzyl or phenethyl.

A particular sub-class of compounds according to the invention is represented by the compounds of formula IIA, and salts and prodrugs thereof:

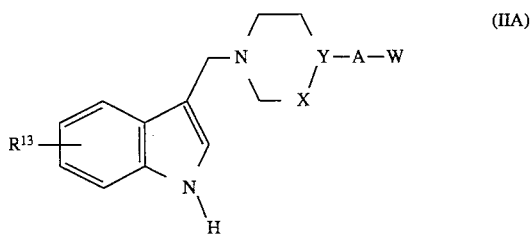

(IIA)

wherein

A represents a moiety of formula —C≡C—, —CH=CH—, —E—(CH$_2$)$_n$— or —(CH$_2$)$_n$—O—;

E represents an oxygen or sulphur atom or a methylene group;

n is 1, 2 or 3;

—X—Y— represents —CH$_2$—CH— or —CH=C—;

W represents a group of formula (i), (ii), (iii), (iv), (v) or (vi):

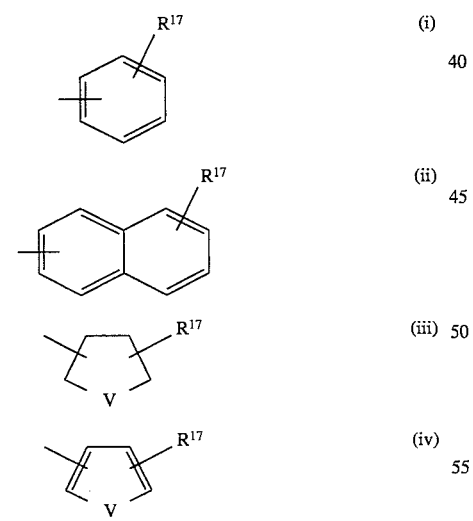

(i)

(ii)

(iii)

(iv)

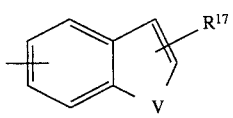

(v)

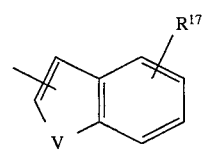

(vi)

in which V represents oxygen, sulphur or NH; and $R^{13}$ and $R^{17}$ independently represent hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$)alkoxy or $C_{2-6}$ alkylcarbonyl.

Particular values of $R^{13}$ include hydrogen, fluoro, chloro, methyl, ethyl, methoxy and benzyloxy.

Particular values of $R^{17}$ include hydrogen, chloro, methoxy and nitro.

One subset of the compounds of formula IIA as defined above is represented by the compounds of formula IIB, and salts and prodrugs thereof:

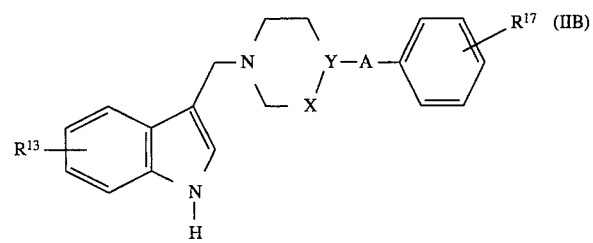

(IIB)

wherein A, X, Y, $R^{13}$ and $R^{17}$ are as defined with reference to formula IIA above.

In a subset of the compounds of formula IIB above, A represents a moiety of formula —E—(CH$_2$)$_n$—, in which E represents an oxygen atom or a methylene group.

Another sub-class of compounds according to the invention is represented by the compounds of formula IIC, and salts and prodrugs thereof:

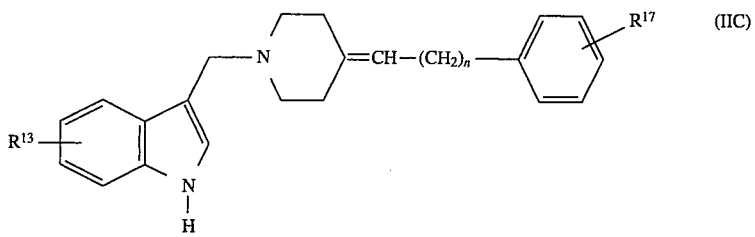

wherein n, $R^{13}$ and $R^{17}$ are as defined with reference to formula IIA above.

Specific compounds within the scope of the present invention include:

3-[4-(2-phenylethyl)piperidin-1-yl]methyl-1H-indole;
3-[4-(2-phenylethyl)-1,2,3,6-tetrahydropyrid-1-yl]methyl-1H-indole;
3-(4-benzyloxypiperidin-1-yl)methyl-1H-indole;
7-chloro-3-[4-(2-phenylethyl)piperidin-1-yl]methyl-1H-indole;
7-chloro-3-[4-(2-phenylethyl)-1,2,3,6-tetrahydropyrid-1-yl]methyl-1H-indole;
(E)-3-[4-(2-phenylethenyl)-1,2,3,6-tetrahydropyrid-1-yl]methyl-1H-indole;
3-[4-(2-phenylethynyl)-1,2,3,6-tetrahydropyrid-1-yl]methyl-1H-indole;
3-(4-phenoxymethyl-1,2,3,6-tetrahydropyrid-1-yl)methyl-1H-indole;
3-(4-benzylthiopiperidin-1-yl)methyl-1H-indole; 7-methoxy-3-[4-(2-phenylethyl)-1,2,3,6-tetrahydropyrid-1-yl]methyl-1H-indole;
6-fluoro-3-[4-(2-phenylethyl)-1,2,3,6-tetrahydropyrid-1-yl]methyl-1H-indole;
3-[4-(3-phenylpropyl)-1,2,3,6-tetrahydropyrid-1-yl]methyl-1H-indole;
3-[4-(3-phenylpropylidene)piperidin-1-yl]methyl-1H-indole;
3-[4-(2-(furan-2-yl)ethyl)-1,2,3,6-tetrahydropyrid-1-yl]methyl-1H-indole;

and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

In the treatment of schizophrenia, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds in accordance with the present invention may be prepared by a process which comprises reacting a compound of formula III with a compound of formula IV:

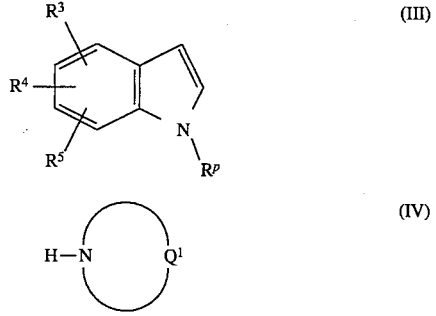

wherein $R^3$, $R^4$ and $R^5$ are as defined above, $Q^1$ represents the residue of a moiety of formula Qa or Qb as defined above, and $R^P$ corresponds to the group R as defined above or represents a suitable protecting group; in the presence of a substantially equimolar amount of formaldehyde; followed, where required, by removal of the protecting group $R^P$; and subsequently, if necessary, N-alkylation by standard methods to introduce the moiety R.

The reaction is conveniently carried out by stirring the reactants in aqueous acetic acid, ideally in the presence of a buffer such as sodium acetate trihydrate, suitably at room temperature.

The formaldehyde may be utilised in the form of paraformaldehyde; or as a solution of formaldehyde in an inert solvent, e.g. 37% aqueous formaldehyde.

The protecting group $R^P$, when present, is suitably an acyl moiety such as acetyl, which can conveniently be removed as necessary by treatment under strongly basic conditions, e.g. sodium methoxide in methanol. Alternatively, the protecting group $R^P$ may be a carbamoyl moiety such as t-butoxycarbonyl (BOC), which can conveniently be removed as necessary by treatment under mildly acidic conditions.

In an alternative procedure, the compounds according to the present invention may be prepared by a process which comprises reacting a compound of formula IV as defined above with a compound of formula V:

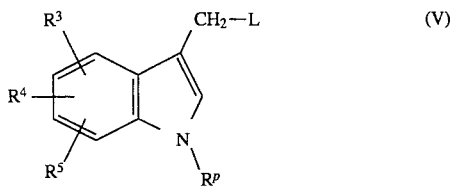

wherein $R^3$, $R^4$, $R^5$ and $R^P$ are as defined above, and L represents a suitable leaving group; followed, where required, by removal of the protecting group $R^P$; and subsequently, if necessary, N-alkylation by standard methods to introduce the moiety R.

The leaving group L is suitably a halogen atom, e.g. chlorine or bromine; or a dialkylamino group, e.g. dimethylamino.

When L represents a halogen atom, the reaction between compounds IV and V is conveniently carried out by stirring the reactants under basic conditions in a suitable solvent, for example potassium carbonate in N,N-dimethylformamide, or triethylamine in tetrahydrofuran or acetonitrile. Where L represents a dialkylamino group, the reaction is conveniently effected by heating the reactants in an inert solvent such as toluene, typically at the reflux temperature of the solvent.

Where they are not commercially available, the starting materials of formula III, IV and V may be prepared by procedures analogous to those described in the accompanying Examples, or by standard methods well known from the art.

It will be appreciated that any compound of formula I initially obtained from any of the above processes may, where appropriate, subsequently be elaborated into a further desired compound of formula I using techniques known from the art. For example, a compound of formula I wherein R is hydrogen initially obtained may be converted into a compound of formula I wherein R represents $C_{1-6}$ alkyl by standard alkylation techniques, such as by treatment with an alkyl iodide, e.g. methyl iodide, typically under basic conditions, e.g. sodium hydride in dimethylformamide, or triethylamine in acetonitrile.

Where the above-described processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques such as preparative HPLC, or the formation of diastereomeric pairs by salt formation with an optically active acid, such as (−)-di-p-toluoyl-d-tartaric acid, and/or (+)-di-p-toluoyl-1-tartaric acid, followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds useful in this invention potently inhibit [$^3$H]-spiperone binding to human dopamine $D_4$ receptor subtypes expressed in clonal cell lines. [$^3$H]—Spiperone Binding Studies Clonal cell lines expressing the human dopamine $D_4$ receptor subtype were harvested in PBS and then lysed in 10 mM Tris-HCl pH 7.4 buffer containing 5 mM $MgSO_4$ for 20 min on ice. Membranes were centrifuged at 50,000g for 15 min at 4° C. and the resulting pellets resuspended in assay buffer (50 mM Tris-HCl pH 7.4 containing 5 mM EDTA, 1.5 mM $CaCl_2$, 5 mM $MgCl_2$, 5 mM KCl, 120 mM NaCl, and 0.1% ascorbic acid) at 20 mg/ml wet weight. Incubations were carried out for 60 min at room temperature (22° C.) in the presence of 0.05–2 nM [$^3$H]-spiperone or 0.2 nM for displacement studies and were initiated by addition of 20–100 µg protein in a final assay volume of 0.5 ml. The incubation was terminated by rapid filtration over GF/B filters presoaked in 0.3% PEI and washed with 10 ml ice-cold 50 mM Tris-HCl, pH 7.4. Specific binding was determined by 10 µM apomorphine and radioactivity determined by counting in a LKB beta counter. Binding parameters were determined by non-linear least squares regression analysis, from which the inhibition constant $K_i$ could be calculated for each test compound.

The compounds of the accompanying Examples were tested in the above assay, and all were found to possess a $K_i$ value for displacement of [$^3$H]-spiperone from the human dopamine $D_4$ receptor subtype of below 1.5 µM.

EXAMPLE 1

3-(4-[2-Phenylethyl]1,2,3,6-tetrahydropyridin-1-yl)methylindole

To a solution of 4-(2-phenylethyl)-1,2,3,6-tetrahydropyridine (prepared by the method of Oediger and Joop, *Leibigs. Ann. Chem.*, 972, 764, 21) (400 mg, 2.2 mmol) in dry toluene (10ml) was added gramine (370 mg, 2.1 mmol) and the reaction heated at reflux overnight. The solvent was evaporated and the residue chromatographed on silica gel eluting with 2% $Et_3N$/EtOAc to give a solid which was recrystallised twice from toluene to yield the title compound as a white solid (160 mg, 25%), m.p. 138–140° C.; (Found: C, 83.59; H, 7.71; N, 8.89. $C_{22}H_{24}N_2$ requires C, 83.50; H, 7.64; N, 8.85%); $\delta_H$ ($CDCl_3$) 2.13 (2H, br s, tetrahydropyridinyl $CH_2$), 2.25 (2H, t, J 8.3 Hz, $PhCH_2CH_2$), 2.64–2.73 (4H, m, tetrahydropyridinyl $CH_2$, $PhCH_2\underline{CH_2}$), 3.05 (2H, br s, tetrahydropyridinyl $CH_2$), 3.81 (2H, s, $N\underline{CH_2}Ar$), 5.40 (1H, br s, tetrahydropyridyl CH), 7.11–7.28 (8H, m, ArH), 7.36 (1H, d, J 7.9 Hz, ArH), 7.72 (1H, d, J 7.9 Hz, ArH), and 8.12 (1H, br s, NH); m/z ($CI^+$, $NH_3$) 317 $(M+1)^+$.

Prepared analogously were:

EXAMPLE 2

3,(4-[2-Phenylethyl]piperidin-1-yl)methylindole

M.p. 142° C. (PhMe); (Found: C, 83.31; H, 8.48; N, 8.71. $C_{22}H_{26}N_2$ requires C, 82.97; H, 8.23; N, 8.80%); $\delta_H$ (DMSO-d$_6$) 1.11–1.16 (3H, m, piperidinyl CH$_2$+CH), 1.46 (2H, m, C$\underline{\text{H}}_2$CH$_2$Ph), 1.64 (2H, d, J 9.5 Hz, piperidinyl CH$_2$), 1.84 (2H, t, J 10.1 Hz, piperidinyl CH$_2$), 2.55 (2H, t, J 7.9 Hz, C$\underline{\text{H}}_2$Ph), 2.85 (2H, d, J 11.1 Hz, piperidinyl CH$_2$), 3.57 (2H, s, N–C$\underline{\text{H}}_2$Ar), 6.93–6.98 (1H, m, indole H), 7.02–7.07 (1H, m, indole H), 7.12–7.14 (4H, m, ArH), 7.22–7.26 (2H, m, ArH), 7.32 (1H, d, J 8.0 Hz, 4-H), 7.60 (1H, d, J 7.8 Hz, 7-H), and 10.86 (1H, br s, NH); m/z (CI$^+$, NH$_3$) 319 (M+1)$^+$.

EXAMPLE 3

3-(4-[Benzyloxy]piperidin-1-yl)methylindole

M.p. 143°–145° C. (EtOAc); (Found: C, 78.49; H, 7.54; N, 8.84. C$_{21}$H$_{24}$N$_2$O requires C, 78.71; H, 7.55; N, 8.74%); $\delta_H$ (DMSO-d$_6$) 1.45–1.51 (2H, m, piperidinyl CH$_2$), 1.82 (2H, m, piperidinyl CH$_2$), 2.07 (2H, t, J 9.7 Hz, piperidinyl CH$_2$), 2.70–2.73 (2H,.m, piperidinyl CH$_2$), 3.34–3.37 (1H, m, piperidinyl CH), 3.59 (2H, s, N–C$\underline{\text{H}}_2$Ar), 4.46 (2H, s, OC$\underline{\text{H}}_2$Ph), 6.94–6.98 (1H, m, indole H), 7.03–7.07 (1H, m, indole H), 7.19 (1H, d, J 2.1 Hz, 2-H), 7.23–7.34 (6H, m, ArH), 7.61 (1H, d, J 7.9 Hz, 7-H), and 10.87 (1H, br s, NH); m/z (CI$^+$, NH$_3$) 321 (M+1)$^+$.

EXAMPLE 4

7-Chloro-3-(4-[2-phenylethyl]piperidin-1-yl)methylindole hydrochloride

Step 1: 7-Chlorogramine

N,N-Dimethylmethylene ammonium chloride (0.94g, 10 mmol) was added to a solution of 7-chloroindole (prepared according to the method of M. Bosco et al, *J. Chem. Soc., Perkin Transactions II*, 1991, 657) (1.31 g, 8.6 mmol) and the mixture stirred at room temperature for 2.5 h. The resulting suspension was diluted with dichloromethane (20 ml), washed with saturated aqueous sodium carbonate (25 ml), and the organic layer dried (Na$_2$CO$_3$) and evaporated to leave an orange solid. Recrystallisation from ethyl acetate gave 7-chlorogramine as pale orange rhombs (0.71 g), m.p. 148°–152° C.; $\delta_H$ (CDCl$_3$) 2.29 (6H, s, NMe$_2$), 3.64 (2H, s, C$\underline{\text{H}}_2$NMe$_2$), 7.06 (1H, t, J 7.8 Hz, 5-H), 7.19 (1H, d, J 7.8 Hz, 6-H), 7.20 (1H, s, 2-H), 7.60 (1H, d, J 7.8 Hz, 4-H), and 8.36 (1H, br s, NH).

Step 2: 7-Chloro-3-(4-[2-phenylethyl]piperidin-1-yl) methylindole hydrochloride

A solution of the aforementioned gramine (208 g, 1 mmol) and 4-(2-phenylethyl)piperidine (200 mg, 1 mmol) in toluene (10 ml) was stirred under reflux for 6.5 h and the solvent removed. The residue remaining was subjected to chromatography on silica gel, eluting with 10% methanol and 1% 880 ammonia in dichloromethane, to give the crude product as a yellow solid. This was dissolved in ether and excess ethereal HCl added, the precipitated solid collected and recrystallised from methanol to give a white solid, m.p. 240°–242° C. (dec.); (Found: C, 76.71; H, 6.89; N, 4.29. C$_{20}$H$_{22}$ClN$_2$ requires C, 77.03; H, 7.11; N, 4.49%); $\delta_H$ (DMSO-d$_6$) 1.41–1.49 (3H, m, piperidinyl CH$_2$ and CH), 1.86 (2H, m, C$\underline{\text{H}}_2$CH$_2$Ph), 2.57 (2H, t, J 7.0 Hz, CH$_2$C$\underline{\text{H}}_2$Ph), 2.88 (2H, m, piperidinyl CH$_2$), 3.16–3.29 (2H, m, piperidinyl CH$_2$), 3.39 (2H, m, piperidinyl CH$_2$), 4.40 (2H, br s, C$\underline{\text{H}}_2$N), 7.10–7.28 (7H, m, ArH), 7.68 (1H, br s, ArH), 7.77 (1H, d, J 8.0 Hz, ArH), and 11.86 (1H, br s, NH); m/z (CI$^+$, NH$_3$) 353 (M+1)$^+$.

EXAMPLE 5

7-Chloro-3-(4-[2-phenylethyl]1-1,2,3,6-tetrahydropyridin-1-yl)methylindole

M.p. 164°–166° C. (PhMe); (Found: C, 75.41; H, 6.55; N, 7.78. C$_{22}$H$_{23}$ClN$_2$ requires: C, 75.31; H, 6.61; N, 7.98%); $\delta_H$ (CDCl$_3$) 2.04 (2H, m, CH$_2$), 2.15–2.19 (2H, m, CH$_2$), 2.49–2.65 (4H, m, 2×CH$_2$), 2.93 (2H, br s, CH$_2$), 3.70 (2H, br s, C$\underline{\text{H}}_2$N), 5.30 (1H, br s, C$\underline{\text{H}}$=CR), 6.93 (1H, t, J 7.7 Hz, 4'-H), 7.04–7.09 (3H, m, ArH), 7.15–7.20 (3H, m, ArH), 7.53 (1H, d, J 7.9 Hz, ArH) and 10.18 (1H, br s, NH); m/z (CI$^+$, NH$_3$) 351 (M+1)$^+$.

EXAMPLE 6

(E)-3-(4-[2-Phenylethenyl]-1,2,3,6-tetrahydropyridin-1-yl)methylindole

M.p. 191°–193° C. (PhMe); (Found: C, 84.12; H, 6.74; N, 8.77. C$_{22}$H$_{22}$N$_2$ requires C, 84.04; H, 7.05; N, 8.91%); $\delta_H$ (CDCl$_3$) 2.43 (2H, br s, CH$_2$), 2.74–2.78 (2H, m, CH$_2$), 3.23 (2H, br s, CH$_2$), 3.86 (2H, s, CH$_2$N), 5.81 (1H, s, C$\underline{\text{H}}$=CR), 6.43 (1H, d, J 16.2 Hz, C$\underline{\text{H}}$=CHPh), 6.78 (1H, d, J 16.3 Hz, CH=C$\underline{\text{H}}$Ph), 7.13–7.31 (6H, m, ArH), 7.37–7.40 (3H, m, ArH), 7.75 (1H, d, J 8.0 Hz, 7-H), and 8.11 (1H, br s, NH); m/z (CI$^+$, NH$_3$) 315 (M+1)$^+$.

EXAMPLE 7

3-(4-[2-Phenylethynyl]-1,2,3,6-tetrahydropyridin-1-yl)methylindole

Step 1: 4-Phenylethynylpyridine

A mixture of 4-bromopyridine hydrochloride (9.75 g, 50 mmol), phenylacetylene (11 ml, 10.2 g; 100 mmol), copper (I) iodide (50 mg) and bis(triphenylphosphino)palladium (II) chloride (200 mg) in dry triethylamine (60 ml) was stirred under reflux for 16 h, the cooled reaction mixture filtered, and the filtrate evaporated. The residual black oil was dissolved in ethyl acetate (100 ml) and washed with saturated aqueous sodium carbonate (2×50 ml) and HCl (1M, 4×25 ml). The acidic washings were extracted with ethyl acetate (2×25 ml) and then basified (5M NaOH). The resulting suspension was extracted with dichloromethane (4×25 ml), the combined organic layers washed with water (25 ml), dried (MgSO$_4$), evaporated, and the residue chromatographed on silica gel, eluting with 7:3 ethyl acetate/60°–80° petrol to give the product as a buff solid (2.79 g, 31%).

Step 2: 1-Benzyl-4-(2-phenylethynyl)-1,2,3,6-tetrahydropyridine

A solution of benzyl bromide (2.0 ml, 2.91 g, 17 mmol) and 4-(2-phenylethynyl)pyridine (2.68 g, 15 mmol) in DMF (10 ml) was stirred for 1 h at 100° C. On cooling, ethanol (65 ml) was added to the resulting paste, followed by portion-wise addition of sodium borohydride (0.76 g, 20 mmol). After stirring for 2 h at room temperature and 1 h at reflux, the mixture was allowed to cool, filtered, and the filtrate evaporated. The residue was partitioned between ethyl acetate (50 ml) and water (2×25 ml), the organic layer dried (MgSO$_4$) and evaporated, and the residue chromatographed, eluting with 15% ethyl acetate in 60°–80° C. petrol, to give the desired product as a pale brown solid (2.49 g, 61% A sample of the hydrogen oxalate was prepared for characterisation; m.p. 217° C. (dec.) (MeOH); (Found: C, 72.80; H, 5.68; N, 13.68. C$_{22}$H$_{21}$NO$_4$ requires C, 72.71; H, 5.82; N, 3.85%).

Step 3: 4-(2-Phenylethynyl)-1,2,3,6-tetrahydropyridine

The aforementioned N-benzyl derivative was debenzylated by the method of Oediger and Joop, *Liebigs Ann, Chim.*, 1972, 764, 21 to give the product as a gum; $\delta_H$ (CDCl$_3$) 2.31–2.35 (2H, m, 3—CH$_2$), 2.55 (1H, br s, NH), 3.05 (2H, t, J 5.7 Hz, 6—CH$_2$), 3.50–3.52 (2H,.m, 2-H), 6.16–6.19 (1H, m, 5-H), 7.29–7.32 (3H, m, 2',4',6'-H), and 7.41–7.44 (2H, m, 3',5'-H).

Step 4: 3-(4-[2-Phenylethynyl]-1,2,3,6-tetrahydropyridin-1-yl) methylindole hydrogen oxalate A solution of 4-(2-phenylethynyl)-1,2,3,6-tetrahydropyridine (177 mg, 0.97 mmol) and gramine (174 mg, 1 mmol) in toluene (15 ml) was stirred under reflux overnight, and the solution then evaporated. The residue was chromatographed, eluting with 10% methanol in dichloromethane to leave the product as a brown gum (262 mg). This was convened to the hydrogen oxalate salt; m.p. 68° C. (dec.) (MeOH/Et$_2$O); (Found: C, 71.64; H, 5.52; N, 6.92. C$_{24}$H$_{22}$N$_2$O$_4$ requires C, 71.63; H, 5.51; N, 6.96%); $\delta_H$ (DMSO-d$_6$) 2.49–2.51 (2H, m, CH$_2$), 3.18 (2H, br s, CH$_2$), 3.63 (2H, m, CH$_2$), 4.35 (2H, br s, CH$_2$N), 6.16 (1H, br s, C$\underline{H}$=CR), 7.07–7.17 (2H, m, ArH), 7.38–7.46 (6H, m, ArH), 7.52 (1H, s, 2-H), 7.75 (1H, d, J 7.7 Hz, 7-H), and 11.39 (1H, br s, NH); m/z (CI$^+$, NH$_3$) 313 (M+1)$^+$.

EXAMPLE 8

3-(4-Phenoxymethyl-1,2,3,6-tetrahydropyridin-1-yl)methylindole

Prepared in an analogous manner to that described for the previous compound. M.p. 140°–142° C. (PhMe); (Found: C, 79.26; H, 6.91; N, 8.57. C$_{21}$H$_{22}$N$_2$O requires C, 79.21; H, 6.96; N, 8.80%); $\delta_H$ (CDCl$_3$) 2.24 (2H, br s, 3'—CH$_2$), 2.69–2.72 (2H, m, 2'—CH$_2$), 3.11 (2H, br s, 6'—CH$_2$), 3.83 (2H, s, C$\underline{H}_2$N), 4.39 (2H, s, C$\underline{H}_2$OPh), 5.77 (1H, t, J 1.4 Hz, C$\underline{H}$=CR), 6.88–6.94 (3H, m, ArH), 7.10–7.37 (5H, m, ArH), 7.36 (1H, dd, J 8.0, 0.7 Hz, 4-H), 7.73 (1H, d, J 7.1 Hz, 7-H), and 8.13 (1H, br s, NH); m/z (CI$^+$, NH$_3$) 319 (M+1)$^+$.

EXAMPLE 9

3-(4-Phenylmethylthiopiperidin-1-yl)methylindole hydrochloride

Step 1: N-Boc-(4-bromo)piperidine

To N-Boc-4-hydroxy piperidine (20 g, 100 mmol) in THF (200 ml) at 0° C. was added triphenylphosphine (28.85 g, 110 mmol) followed by carbon tetrabromide (36.48 g, 110 mmol). The solution was stirred at room temperature for 2 h then filtered and concentrated under vacuum. Flash column chromatography using dichloromethane in hexane (10–70%) yielded the product as a colourless oil (23.6 g); $\delta_H$ (CDCl$_3$) 1.47 (9H, s, t-Bu), 1.93 and 2.04 (4H, m, 3,5-piperidinyl CH$_2$), 3.31 and 3.66 (4H, m, 2,6-piperidinyl CH$_2$), and 4.39 (1H, m, 4-piperidinyl H).

Step 2: N-Boc-4-benzylthiopiperidine

To benzyl mercaptan (17 ml, 152 mmol) in dimethylformamide at 0° C. under nitrogen was added sodium hydride (80% dispersion in mineral oil, 4.38 g, 152 mmol) the solution was stirred at room temperature for 15 minutes then cooled to 0° C. prior to adding N-Boc-(4-bromo)piperidine (10.8 g, 38 mmol). The mixture was stirred for 14 h at room temperature then poured into water (50 ml), extracted with diethyl ether (2×100 ml), the organic layers combined, dried (MgSO$_4$), filtered, evaporated, and the crude product purified by flash column chromatography using 10% ethyl acetate in hexane to yield the product as a pale yellow oil (2.86 g); $\delta_H$ (CDCl$_3$) 1.46 (9H, s, t-Bu), 1.51 and 1.87 (4H, m, 3,5-piperidinyl CH$_2$), 2.85 and 3.91 (4H, m, 2,6-piperidinyl CH$_2$), 2.69 (1H, m, 4-piperidinyl H), 3.77 (2H, s, SC$\underline{H}_2$), and 7.24–7.32 (5H, m, ArH).

Step 3: 3-(4-Phenylmethylthiopiperidin-1-yl)methylindole hydrochloride

To N-Boc-4-benzylthiopiperidine (0.60 g, 1.98 mmol) in diethyl ether was added hydrogen chloride in diethyl ether (3 ml, ~2.5 mmol) dropwise and the solution allowed to stir for 5 minutes then concentrated under vacuum and the residue partitioned between saturated sodium hydrogen carbonate solution and dichloromethane, the organic layer dried over magnesium sulphate, filtered and evaporated to dryness. To the residue in dry toluene (50 ml) was added gramine (0.35 g, 2 mmol) and the mixture stirred at reflux under nitrogen for 6 h, evaporated and the residue redissolved in 1:1 methanol and diethyl ether (10 ml), hydrogen chloride in diethyl ether (3 ml, ~2.5 mmol) added dropwise and the solution stirred for 5 minutes, partially evaporated and triturated with diethyl ether. The white precipitate formed was collected and recrystallised from methanol/diethyl ether to yield the product (90 mg) as a white solid, m.p. 264–266° C.; (Found: C, 66.61; H, 6.26; N, 7.26; C$_{21}$H$_{24}$N$_2$S1.2HCl requires C, 66.33; H, 6.60; N, 7.36%); $\delta_H$ (DMSO-d$_6$) 1.73 and 2.07 (4H, m, 3,5-piperidinyl CH$_2$), 2.70 (1H, m, 4-piperidinyl H), 2.91 and 3.42 (4H, m, 2,6-piperidinyl CH$_2$), 3.78 (2H, s, SC$\underline{H}_2$), 4.41 (2H, s, NC$\underline{H}_2$Ar), and 7.08–7.82 (9H, m, ArH); m/z (CI$^+$, NH$_3$ 336 (M+1)$^+$.

EXAMPLE 10

7-Methoxy-3-(4-[2-phenylethyl]-1,2,3,6-tetrahydropyridin-1-yl)methylindole

M.p. 131°–133° C. (PhMe); (Found: C, 79.63; H, 7.47; N, 7.88. C$_{23}$H$_{26}$NO requires C, 79.73; H, 7.56; N, 8.09%); $\delta_H$ (CDCl$_3$) 2.16 (2H, br s, tetrahydropyridinyl 3—CH$_2$), 2.26 (2H, t, J 7.3 Hz, tetrahydropyridinyl 2-CH$_2$), 2.69–2.73 (4H, m, PhC$\underline{H}_2$C$\underline{H}_2$), 3.08 (2H, br s, tetrahydropyridinyl 6-CH$_2$), 3.84 (2H, s, NC$\underline{H}_2$Ar), 3.96 (3H, s, OCH$_3$), 5.39 (1H, br s, C$\underline{H}$=CR), 6.65 (1H, d, J 7.7 Hz, ArH), 7.05 (1H, t, J 7.9 Hz, ArH), 7.15–7.18 (3H, m, ArH), 7.24–7.30 (4H, m, ArH), and 8.34 (1H, br s, NH); m/z (CI$^+$, NH$_3$) 347 (M+1)$^+$.

EXAMPLE 11

6-Fluoro-3-(4-[2-phenylethyl]-1,2,3,6-tetrahydropyridin-1-yl)methylindole

M.p. 150°–152° C. (PhMe); (Found: C, 79.33; H, 6.68; N, 7.93. C$_{22}$H$_{23}$FN$_2$ requires C, 79.01; H, 6.93; N, 8.37%); $\delta_H$ (CDCl$_3$) 2.13 (2H, br s, tetrahydropyridinyl 3-CH$_2$), 2.26 (2H, t, J 8.2 Hz, PhCH$_2$C$\underline{H}_2$), 2.61–2.64 (2H, m, tetrahydropyridinyl 2-CH$_2$), 2.71 (2H, t, J 8.2 Hz, PhC$\underline{H}_2$CH$_2$), 3.02 (2H, br s, tetrahydropyridinyl 6-CH$_2$), 3.77 (2H, s, NC$\underline{H}_2$Ar), 5.39 (1H, br s, tetrahydropyridinyl 5-CH), 6.88 (1H, t, J 8.0 Hz, ArH), 7.03 (1H, d, J 9.6 Hz, ArH), 7.15–7.17 (4H, m, ArH), 7.24–7.28 (2H, m, ArH), 7.61–7.65 (1H, m, ArH), and 8.08 (1H, br s, NH); m/z (CI$^+$, NH$_3$), 335 (M+1)$^+$.

EXAMPLE 12

3-(4-[3-Phenylpropyl]-1,2,3,6-tetrahydropyridin-1-yl)methylindole oxalate

M.p. 171°–172° C. (dec.) (EtOAc); (Found: C, 71.39; H, 6.78; N, 6.59. C$_{23}$H$_{26}$N$_2$.(CO$_2$H)$_2$ requires C, 71.41; H, 6.71; N, 6.66%); $\delta_H$ (DMSO-d$_6$) 1.67 (2H, m, PhCH$_2$C$\underline{H}_2$CH$_2$), 2.01 (2H, t, J 7.2 Hz, CH$_2$), 2.25 (2H, s, tetrahydropyridinyl CH$_2$), 2.54 (2H, m, CH$_2$), 3.21 (2H, br s, tetrahydropyridinyl CH$_2$), 3.56 (2H, s, tetrahydropyridinyl CH$_2$) 4.41 (2H, s, NC$\underline{H}_2$Ar), 5.39 (1H, s, tetrahydropyridinyl CH), 7.07–7.18 (5H, m, ArH), 7.23–7.27 (2H, m, ArH), 7.44 (1H, d, J 7.9 Hz, 4-H), 7.54 (1H, d, J 2.1 Hz, 2-H), 7.74 (1H, d J 7.7 Hz, 7-H), and 11.46 (1H, br s, NH); m/z (CI$^+$, NH$_3$) 331 (M+1)$^+$.

EXAMPLE 13

3-(4-[3-Phenylpropylidene]piperidin-1-yl)methylindole oxalate

M.p. 170°–171° C. (dec.) (EtOH); (Found: C, 71.10; H, 6.67; N, 6.54. $C_{23}H_{26}N_2 \cdot (CO_2H)_2$ requires C, 71.41; H, 6.71; N, 6.66%); $\delta_H$ (DMSO-d6) 2.26 (6H, m, 3×CH$_2$), 2.57 (2H, t, J 7.3 Hz, CH$_2$), 2.80–3.00 (4H, m, 2×CH$_2$), 4.32 (2H, s, N—CH$_2$), 5.27 (1H, t, J 7.2 Hz, PhCH$_2$CH$_2$C$\underline{H}$), 7.03–7.18 (7H, m, ArH), 7.45 (1H, d, J 8.0 Hz, 4-H), 7.50 (1H, s, 2-H), 7.71 (1H, d, J 7.8 Hz, 7-H), and 11.47 (1H, br s NH); m/z (CI−, NH$_3$) 329 (M−1)$^+$.

EXAMPLE 14

3-(4-[2-(Furan-2-yl)ethyl]-1,2,3,6-tetrahydropyridin-1-yl)methylindole hydrochloride Step 1: (E)-1-(Pyridin-4-yl)-2-(furan-2-yl)ethene A solution of 4-methylpyridine (15 g, 0.16 mol) in acetic anhydride (100 ml) was treated with 2-furaldehyde (15.5 g, 0.16 mol) and heated at reflux for 16 hrs. The solvent was evaporated to give a black oil which was treated with water (30 ml) and stirred for 30 mins at room temperature. Ethyl acetate (150 ml) and saturated sodium carbonate (100 ml)were then added and the stirring continued for 30 mins. The solvents were decanted to leave a black oily residue which was retained (A). From the decanted solvents the organic phase was separated, dried (Na$_2$SO$_4$) and evaporated to give a black oil (B). The oily residue (A) was dissolved in dichloromethane (150 ml), washed with saturated sodium carbonate solution (100 ml), dried (Na$_2$SO$_4$) and evaporated to give a black oil which was combined with oil (B). The mixture was chromatographed with a gradient of ethyl acetate in hexane (50% –100%) as eluant to afford the title compound as a brown solid (9.8 g, 36%); $\delta_H$ (DMSO-d6) 6.58–6.64 (1H, m, furanyl H), 6.66–6.72 (1H, m, furanyl H), 6.96 (1H, d, J 17.5 Hz, ArC$\underline{H}$=CHAr'), 7.42 (1H, d, J 17.5 Hz, ArCH=C$\underline{H}$Ar'), 6.50–6.58 (2H, m, pyridinyl H), 7.78–7.82 (1H, m, furanyl H), and 8.50–8.57 (2H, m, pyridinyl H).

Step 2: 1-(Pyridin-4-yl)-2-(furan-2-yl)ethane

A solution of the foregoing compound (8 g, 46.8 mmol) in methanol (200 ml) was treated with ammonium formate (14.7 g, 234.0 mmol). 10% Palladium on charcoal catalyst (400 mg) was added and the mixture was stirred at reflux for five hours. The catalyst was filtered off and the solvent evaporated. The residue was partitioned between dichloromethane and water. The organic layer was separated, dried (MgSO$_4$) and evaporated to give a beige oil. This material was chromatographed with a gradient of ethyl acetate in hexane (50% –100%) as eluant to afford the title compound as a colourless oil (2.5 g, 31%); $\delta_H$ (DMSO-d6) 2.94–3.06 (4H, m, 2×CH$_2$), 6.06–6.12 (1H, m, furanyl H), 6.32–6.38 (1H, m, furanyl H), 7.20–7.28 (2H, m, pyridinyl H), 7.50–7.56 (1H, m, furanyl H), and 8.40–8.50 (2H, m, pyridinyl H).

Step 3: 1-Benzyl-4-[2-(furan-2-yl)ethyl]-1,2,3,6-tetrahydropyridine

A solution of 1-(pyridinyl)-2-(furan-2-yl)ethane (2 g, 11.6 mmol) in anhydrous dimethylformamide (5 ml)was treated with benzyl bromide (1.5 ml, 12.7 mmol) and the reaction stirred at room temperature for one hour. The reaction was diluted with ethanol (50 ml), treated with sodium borohydride (0.55 g, 14.5 mmol) and heated at reflux for one hour. The solvent was evaporated and the residue partitioned between ethyl acetate and water. The organic layer was separated, dried (Na$_2$SO$_4$) and evaporated to give crude product as a yellow oil. This material was triturated with diethyl ether to afford the title compound (2.3 g, 68%) as a colourless solid; $\delta_H$ (DMSO-d6) 1.92–2.10 (2H, m, tetrahydropyridinyl CH$_2$), 2.14–2.30 (2H, m, C$\underline{H}_2$CH$_2$), 2.36–2.50 (2H, m, CH$_2$C$\underline{H}_2$), 2.60–2.82 (2H, m, tetrahydropyridinyl CH$_2$), 2.84–2.90 (2H, m, tetrahydropyridinyl CH$_2$), 3.50 (2H br s, ArC$\underline{H}_2$N), 5.32–5.44 (1H, m, tetrahydropyridinyl 5-H), 6.02–6.10 (1H, m, furanyl H), 6.30–6.36 (1H, m, furanyl H), 7.16–7.36 (5H, m, ArH), and 7.44–7.52 (1H, m, furanyl H); m/z (CI$^+$, NH$_3$) 268 (M+1)$^+$.

Step 4-[2-(Furan-2-yl)ethyl]-1,2,3,6-tetrahydropyridine

A cooled (0° C.) solution of the product from the previous step (1.8 g, 6.8 mmol) in anhydrous dichloromethane (20 ml) was treated with 2-chloroethylchloroformate (0.45 ml, 8.8 mmol) dropwise. The mixture was stirred for 1 hr at 0° C. The solvent was evaporated and the residue dissolved in methanol (60 ml). This solution was heated at reflux for one hour whereupon the solvent was evaporated. The residue was partitioned between dichloromethane and saturated aqueous potassium carbonate solution. The organic phase was separated, dried (Na$_2$SO$_4$) and evaporated to give the title compound (867 mg, 72%) as a colourless oil; $\delta_H$ (DMSO-d6) 1.84–1.96 (2H, m, tetrahydropyridinyl CH$_2$), 2.16–2.30 (2H, m, CH$_2$C$\underline{H}_2$), 2.64–2.80 (4H, m, tetrahydropyridinyl CH$_2$ and C$\underline{H}_2$CH$_2$), 3.06–3.10 (2H, m, tetrahydropyridinyl CH$_2$), 5.40–5.46 (1H, m, tetrahydropyridinyl 5-H), 6.06–6.12 (1H, m, furanyl H), 6.32–6.38 (1H, m, furanyl 5-H), and 7.48–7.56 (1H, m, furanyl H).

Step 5: 3-(4-[2-(Furan-2-yl)ethyl]-1,2,3,6tetrahydropyridin-1-yl)methylindole hydrochloride A solution of gramine (775 mg, 4.5 mmol) and 4-[2-(furan-2-yl)ethyl]-1,2,3,6-tetrahydropyridine (867 mg, 4.9 mmol) in anhydrous toluene (50 ml) was heated at reflux for sixteen hours. The solvent was evaporated and the residue chromatographed with a gradient of methanol in dichloromethane (1–10%) as eluant. The product was dissolved in dichloromethane (30 ml) and treated with ethereal hydrogen chloride. The solvents were evaporated and the residue triturated with diethyl ether to afford the title compound (272 mg, 15%) as a colourless solid; m.p. 155°–156° C.; (Found: C, 69.09; H, 6.83; N, 7.88. $C_{20}H_{22}N_2O \cdot HCl \cdot 0.25H_2O$ requires C, 69.15; H, 6.82; N, 8.06% ); $\delta_H$ (DMSO-d$_6$) 2.20–2.50 (4H, m, tetrahydropyridinyl CH$_2$ and CH$_2$C$\underline{H}_2$), 2.72 (2H, t, J 7.5 Hz, C$\underline{H}_2$CH$_2$), 3.00–3.10 (1H, m, tetrahydropyridinyl CH$_2$), 3.40–3.70 (3H, m, tetrahydropyridinyl CH$_2$), 4.46 (2H, d, J 4.7 Hz, ArC$\underline{H}_2$), 5.40–5.45 (1H, m, tetrahydropyridinyl 5-H), 6.12 (1H, d, J 2.3 Hz, furanyl H), 6.32–6.34 (1H, m, furanyl H), 7.04–7.20 (2H, m, ArH), 7.40–7.50 (2H, m, ArH), 7.65 (1H, d, J 2.7 Hz, ArH), 7.78 (1H, d, J 7.8 Hz, ArH), 10.40 (1H, br s, NH), and 11.53 (1H, s, NH$^+$); m/z (CI$^+$, NH$_3$) 307 (M+1)$^+$.

We claim:

1. A compound of formula I, or a salt or prodrug thereof:

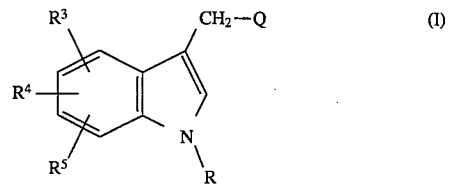

wherein

R represents hydrogen or $C_{1-6}$ alkyl;

Q represents a moiety of formula Qa or Qb:

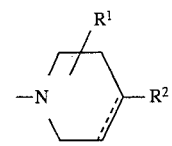
(Qa)

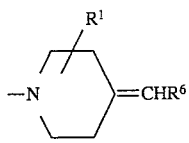
(Qb)

in which the broken line represents an optional chemical bond;

$R^1$ represents hydrogen, or an optionally substituted $C_{1-6}$ alkyl, $C_{1-6}$ alkoxy, $C_{2-6}$ alkenyl, $C_{2-6}$ alkynyl, aryl, aryl($C_{1-6}$) alkyl, aryloxy($C_{1-6}$) alkyl, aryl($C_{1-6}$)alkoxy, aryl($C_{1-6}$)alkylthio, aryl($C_{2-6}$)alkenyl, aryl($C_{2-6}$)alkynyl, $C_{3-7}$ heterocycloalkyl($C_{1-6}$)alkyl, heteroaryl, heteroaryl($C_{1-6}$)alkyl, heteroaryl($C_{2-6}$)alkenyl or heteroaryl($C_{2-6}$)alkynyl group;

$R^2$ represents an optionally substituted $C_{1-6}$ alkoxy, $C_{2-6}$ alkenyl, $C_{2-6}$ alkynyl or $C_{3-7}$ heterocycloalkyl($C_{1-6}$)alkyl group; or aryl($C_{2-6}$)alkyl, aryloxy($C_{1-6}$)alkyl, aryl($C_{1-6}$)alkoxy, aryl($C_{1-6}$)alkylthio, aryl($C_{2-6}$)alkenyl, aryl($C_{2-6}$)alkynyl, heteroaryl($C_{2-6}$)alkyl, heteroaryl($C_{2-6}$)alkenyl or heteroaryl($C_{2-6}$)alkynyl, any of which groups may be optionally substituted on the aromatic moiety;

$R^6$ represents an optionally substituted $C_{1-6}$ alkyl, $C_{1-6}$ alkoxy, $C_{2-6}$ alkenyl, $C_{2-6}$ alkynyl, aryl, aryl($C_{1-6}$)alkyl, aryloxy($C_{1-6}$)alkyl, aryl($C_{1-6}$)alkoxy, aryl($C_{1-6}$)alkylthio, aryl($C_{2-6}$)alkenyl, aryl($C_{2-6}$)alkynyl, $C_{3-7}$ heterocycloalkyl($C_{1-6}$)alkyl, heteroaryl, heteroaryl($C_{1-6}$)alkyl, heteroaryl($C_{2-6}$)alkenyl or heteroaryl($C_{2-6}$)alkynyl group;

$R^3$, $R^4$ and $R^5$ independently represent hydrogen, hydrocarbon, a heterocyclic group, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$ or —$CONR^aR^b$; and $R^a$ and $R^b$ independently represent hydrogen, hydrocarbon or a heterocyclic group.

2. A compound represented by formula IIA, or salts or prodrugs thereof:

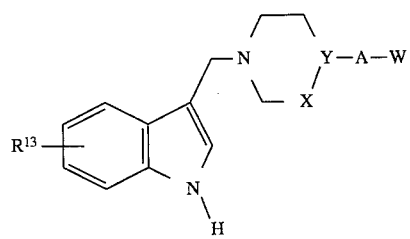
(IIA)

wherein

A represents a moiety of formula —C≡C—, —CH=CH—, —E—(CH$_2$)$_n$— or —(CH$_2$)$_n$—O—;

E represents an oxygen or sulphur atom or a methylene group;

n is 1, 2 or 3;

—X—Y— represents —CH$_2$—CH— or —CH=C—;

W represents a group of formula (i), (ii), (iii), (iv), (v) or (vi):

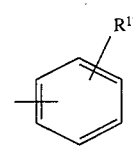
(i)

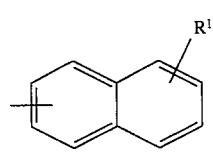
(ii)

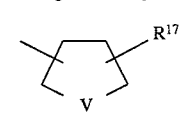
(iii)

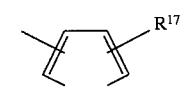
(iv)

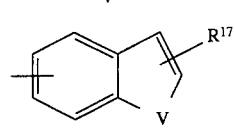
(v)

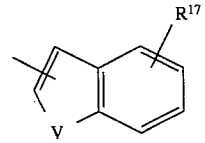
(vi)

in which V represents oxygen, sulphur or NH; and $R^{13}$ and $R^{17}$ independently represent hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$)alkoxy or $C_{2-6}$ alkylcarbonyl.

3. A compound as claimed in claim 2 represented by formula IIB, or pharmaceutically acceptable salts or prodrugs thereof:

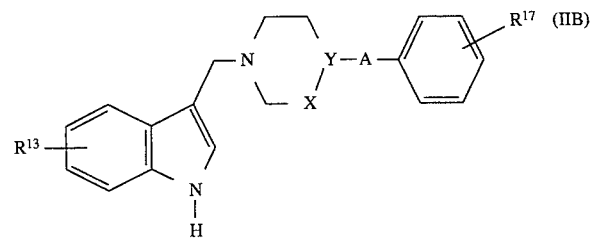
(IIB)

wherein A, X, Y, $R^{13}$ and $R^{17}$ are as defined in claim 2.

4. A compound as claimed in claim 1 represented by formula IIC or, and salts or prodrugs thereof:

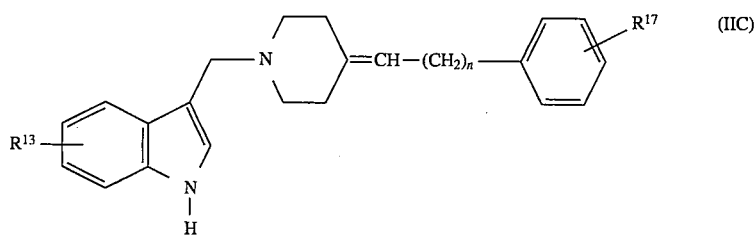

wherein n is 1, 2 or 3;

R$^{13}$ and R$^{17}$ independently represent hydrogen, halogen, cyano, nitro, trifluoromethyl, amino, C$_{1-6}$ alkylamino, de(C$_{1-6}$)alkylamino, C$_{1-6}$ alkyl, C$_{1-6}$ alkoxy, aryl(C$_{1-6}$)alkoxy or C$_{2-6}$ alkylcarbonyl.

5. A compound as claimed in claim 2 wherein R$^{13}$ represents hydrogen, fluoro, chloro, methyl, ethyl, methoxy or benzyloxy.

6. A compound as claimed in claim 2 wherein R$^{17}$ represents hydrogen, chloro, methoxy or nitro.

7. A compound as claimed in claim 1 selected from:
3-[4-(2-phenylethyl)piperidin-1-yl]methyl-1H-indole;
3-[4-(2-phenylethyl)-1,2,3,6-tetrahydropyrid-1-yl]methyl-1H-indole;
3-(4-benzyloxypiperidin-1-yl)methyl-1H-indole;
7-chloro-3-[4-(2-phenylethyl)piperidin-1-yl]methyl-1H-indole;
7-chloro-3-[4-(2-phenylethyl)-1,2,3,6-tetrahydropyrid-1-yl]methyl-1H-indole;
(E)-3-[4-(2-phenylethenyl)-1,2,3,6-tetrahydropyrid-1-yl]methyl-1H-indole;
3-[4-(2-phenylethynyl)-1,2,3,6-tetrahydropyrid-1-yl]methyl-1H-indole;
3-(4-phenoxymethyl-1,2,3,6-tetrahydropyrid-1-yl)methyl-1H-indole;
3-(4-benzylthiopiperidin-1-yl)methyl-1H-indole;
7-methoxy-3-[4-(2-phenylethyl)-1,2,3,6-tetrahydropyrid-1-yl]methyl-1H-indole;
6-fluoro-3-[4-(2-phenylethyl)-1,2,3,6-tetrahydropyrid-1-yl]methyl-1H-indole;
3-[4-(3-phenylpropyl)-1,2,3,6-tetrahydropyrid-1-yl]methyl-1H-indole;
3-[4-(3-phenylpropylidene)piperidin-1-yl]methyl-1H-indole; and
3-[4-(2-(furan-2-yl)ethyl)-1,2,3,6-tetrahydropyrid-1-yl]methyl-1H-indole;

or salts or prodrugs thereof.

8. A pharmaceutical composition comprising a compound as claimed in claim 1 in association with a pharmaceutically acceptable carrier.

9. A method for the treatment and/or prevention of schizophrenia, which method comprises administering to a patient in need of such treatment an effective amount of a compound as claimed in claim 1.

* * * * *